United States Patent
Abraham et al.

(10) Patent No.: US 6,954,267 B2
(45) Date of Patent: Oct. 11, 2005

(54) DEVICE FOR MEASURING SURFACE DEFECTS

(75) Inventors: Michael Abraham, Mainz (DE); Andreas Lang, Frankfurt (DE); Michael Schweiger, Orlamunde (DE)

(73) Assignee: Nanophotonics AG, Mainz (DE)

(*) Notice: Subject to any disclaimer, the term of this patent is extended or adjusted under 35 U.S.C. 154(b) by 361 days.

(21) Appl. No.: 10/237,909

(22) Filed: Sep. 9, 2002

(65) Prior Publication Data
US 2003/0193666 A1 Oct. 16, 2003

Related U.S. Application Data

(63) Continuation-in-part of application No. 10/120,641, filed on Apr. 11, 2002, now Pat. No. 6,798,513.

(51) Int. Cl.[7] .................................................. G01N 21/00
(52) U.S. Cl. ........................................................ 356/237.2
(58) Field of Search ..................... 250/559.41, 559.45, 250/559.46; 356/237.2, 237.3, 237.4, 237.5

(56) References Cited

U.S. PATENT DOCUMENTS

| | | | |
|---|---|---|---|
| 3,736,432 A | * | 5/1973 | Sweet .......................... 377/10 |
| 4,155,098 A | * | 5/1979 | Roach et al. ............. 356/237.5 |
| 4,314,763 A | | 2/1982 | Steigmeier et al. |
| 4,363,118 A | * | 12/1982 | Roach et al. ............. 356/237.5 |
| 4,508,450 A | * | 4/1985 | Ohshima et al. ......... 356/237.2 |
| 4,832,487 A | | 5/1989 | Mikuriya et al. |
| 4,954,723 A | | 9/1990 | Takahashi et al. |
| 5,377,002 A | | 12/1994 | Malin et al. |
| 5,502,567 A | | 3/1996 | Pokrowsky et al. |
| 5,644,393 A | * | 7/1997 | Nakamura et al. ....... 356/237.3 |
| 5,808,990 A | * | 9/1998 | Summers ................... 369/53.2 |
| 5,814,829 A | * | 9/1998 | Broude et al. ......... 250/559.46 |
| 5,867,276 A | * | 2/1999 | McNeil et al. .............. 356/445 |
| 5,892,577 A | * | 4/1999 | Gordon ....................... 356/73 |
| 6,091,499 A | | 7/2000 | Abraham et al. |
| 6,104,481 A | | 8/2000 | Sekine et al. |
| 6,181,427 B1 | | 1/2001 | Yarussi et al. |
| 6,185,030 B1 | * | 2/2001 | Overbeck .................... 359/225 |
| 6,421,112 B1 | * | 7/2002 | Bisschops et al. ............ 355/53 |
| 2003/0048448 A1 | * | 3/2003 | Fleming et al. ............. 356/423 |
| 2003/0089608 A1 | * | 5/2003 | Kumekawa ................. 204/471 |

FOREIGN PATENT DOCUMENTS

| | | |
|---|---|---|
| DE | 37 31 862 | 6/1988 |
| DE | 39 19 330 | 12/1989 |
| EP | 0 499 312 | 2/1991 |
| EP | 1 318 392 | 6/2003 |
| RU | 2064670 | 4/1993 |
| WO | 0 624 787 A1 | 11/1994 |
| WO | WO 00/33055 | 6/2000 |

* cited by examiner

*Primary Examiner*—Michael P. Stafira
*Assistant Examiner*—Juan D. Valentin, II
(74) *Attorney, Agent, or Firm*—Hudak, Shunk & Farine Co. LPA

(57) ABSTRACT

In view of the miniaturization of semiconductor components, the prevention of particles and other defects on the wafer surface during production is of great importance. The inspection should proceed as process-oriented as possible. For this purpose, devices are needed which on the one hand, are of very compact construction, while on the other hand, they still are equipped with measuring systems meeting the highest requirements.

The device according to the invention for measuring surface defects, comprising a sample holder, a rotation drive for the sample holder, wherein the rotational axis runs perpendicular to the sample surface to be measured, an optical measuring system (10) for measuring scattered light, as well as at least one linear drive (23) for the measuring system, wherein the rotational direction is radial to the rotational axis of the sample holder, is capable of scanning the entire sample surface (16). By moving not only the sample, but also the measuring system, the need for space as a whole is reduced and the total device can be constructed with a more compact design.

18 Claims, 9 Drawing Sheets ial defects at the sample surface, by a process different from that of the first measuring system. Since large and small particles scatter the light in different manners, this makes it possible to adapt the measuring system to differently sized particles in optimum fashion.

DEVICE FOR MEASURING SURFACE DEFECTS

CROSS REFERENCE

This application is a Continuation-In-Part of U.S. Ser. No. 10/120,641, filed Apr. 11, 2002, now U.S. Pat. No. 6,798,513, for Measuring Module, herein fully incorporated by reference.

FIELD OF THE INVENTION

The invention relates to a device for measuring surface defects.

In view of the miniaturization of semiconductor components, the prevention of particles and other defects on the wafer surface during production is of great importance. Since a particle grain can by now be larger than an entire circuitry, even the smallest defects lead to a large amount of waste.

BACKGROUND OF THE INVENTION

In general, scattered light is used for measuring defects on smooth surfaces. For this purpose, the surface of, for example, a wafer is illuminated with a laser beam. The scatter characteristics of different particle sizes are shown in FIG. 1. A small particle 2 as well as a large particle 3 are illuminated with a laser beam 1. 'Small particle' means that the particle diameter is much smaller than the wavelength used. 'Large particle' means that the particle diameter is approximately of the same size as the wavelength or a little larger. As shown in FIG. 1, small particles scatter in isotropic manner into the space. Large particles, on the other hand, generate strong backscattering; see also scatter ellipse 4.

All methods of detecting surface defects are based on the detection of the scattered radiation, while blanking out the primary light reflected by a mirror. The intensity of the scattered light usually lies several levels below that of the reflected primary light.

Patent application U.S. Pat. No. 5,377,002 describes an apparatus for measuring scattered light, wherein the scattered light is focused through a converging lens onto a photo detector. In this process, the converging lens defines the acceptance angle before the scattered light. Directly reflected light is blanked out.

Patent application RU 2064670 proposes to collect the scattered light by means of an elliptical mirror disposed in rotational symmetry around the incident beam. Due to the very large acceptance angle, this apparatus is particularly sensitive to small particles.

Patent application WO 00/33055, as well, uses either ellipsoid or paraboloid, rotationally symmetrical mirrors, in order to collect the scattered light. However, the reflected primary light is not blanked out, but the scattered light is deflected via a deflection mirror. The incident and the reflected primary beams enter through an opening in the deflecting mirror. This apparatus, as well, is particularly sensitive to small particles.

Patent application EP 0624787 A1 proposes, in order to enhance the measuring sensitivity for large particles as well, to place two converging lenses in the path of the primary light beam within the ellipsoid rotationally symmetrical mirror, in order to be able to also detect the strong backscattering occurring with large particles. The primary light is blanked out again in front of the detector. This apparatus however has the disadvantage that scattered light is generated also at both converging lenses, which as a whole corrupts the measuring results. Furthermore, the focus is always on measuring the scattered light in its entirety, rather than on differentiating it based on particle size.

Since with all detection methods described the light spot can always only illuminate a fraction of the sample surface, the entire sample surface has to be scanned. This may be achieved with a rectangular grid, for example. With circular samples, such as wafers, a spiral-shaped scanning path as described in the patent application U.S. Pat. No. 4,314,763 is best suited. With this method, the sample is either rotated around its axis while simultaneously undergoing a translational movement in radial direction and while the light beam remains stationary, or the sample remains immobile and the spiral-form movement is executed by the light beam, which in very sensitive optical systems impairs the measuring accuracy.

Patent application WO 00/33055 further develops the spiral scan principle into the so-called record player principle. With this method, the sample surface is rotated around a first rotational axis. The light beam, meanwhile, travels on an arc around a second rotational axis. It swings over the sample surface just like the sensing head of a record player. This record player principle has prevailed on the market and is already used in the process-oriented quality surveillance for semiconductor components (e.g. device "Reflex 300" of the "Reflex" company, Moscow).

The apparatus already on the market has the disadvantage that the measuring head has to be kept very small, in order to allow for the swinging motion. This leaves very little space for the optical system so that it has to be very simple. For example, only very simple miniature diode lasers can be used as they work within the red spectral range. Since blue lasers require more space, the resolution cannot be further improved in these devices.

SUMMARY OF THE INVENTION

Based on the preceding explanations, the present invention has the object of providing a device for measuring surface defects, which device can be used for process-oriented quality surveillance while still meeting the highest technical measuring requirements.

This object is achieved by a device according to the claims.

The device according to the invention for measuring surface defects, comprising a sample holder, a rotation drive for the sample holder with its rotational axis perpendicular to the sample surface to be measured, an optical measuring system for scattered light measurements, as well as at least one linear drive for the measuring system with its rotational direction radial to the rotational axis of the sample holder, is capable of scanning the entire sample surface. By not only moving the sample, but also the measuring system, less space is needed as a whole and the entire device can be constructed in a more compact form. This makes the device particularly suitable for process-oriented quality surveillance, since it can simply be integrated into existing process facilities.

In the device according to the invention, a compact construction is achieved less by the excessive miniaturization of the measuring system, as for example in devices operating on the basis of the "record player principle", than by the fact that—as already explained—the sample to be measured is just rotated and the measuring system is moved radially to the rotational axis across the sample surface with the aid of a linear drive.

In a preferred embodiment, the device is to be provided with a second measuring system for measuring any additional physical property, wherein the two measuring systems are disposed at a fixed distance from one another and one behind the other in translational direction. Particularly preferred in this context is the combination of a scattered light measurement for large particles with the scattered light measurement for small particles.

In a refinement of the optical measuring system, use of a diaphragm before the scattered light deflecting unit optimizes the collection of light at smaller angles to the emerging beam, which leads to a high measuring sensitivity for large particles. The diaphragm is dimensioned in such a way that light is projected onto the deflecting unit at small angles and detected. By dimensioning the diaphragm in this way it becomes possible to define the dihedral angle measured by the detector. Furthermore, by using a diaphragm a smaller degree of parasitic scattered light can be achieved than is possible with the conventional refractive optical systems.

Preferably, the scattered light deflecting unit is constructed as a mirror which has an opening for the primary light and only reflects the scattered radiation. With this method, only the scattered light at the smallest angle is not detected by the scattered light signal. The use of a reflective element as scattered light deflecting unit, just like the diaphragm, has the advantage of providing a good signal-to-noise ratio.

For optimally measuring the scattered radiation, it has proven advantageous to have the light beam of the light source fall essentially perpendicular onto the surface to be measured. The measuring system can be dimensioned in a way to achieve a compact construction and is easy to adjust. In some applications, however, it may be advantageous to select a more grazing angle of incidence, in order, for example, to better be able to detect scratches.

In context with the detection of particles, the question of the nature of the particles is often asked. One measuring system alone is not capable, for example, of differentiating between external particles and embedded particles or indentations. A second measuring system using a different type of surface illumination can offer additional information.

This second measuring system could, for example, be a dark field microscope. Equally, the second measuring system can be used to measure a completely different physical property, such as the distribution of layer thickness with the aid of a spectrometer. The information of the two measuring systems is provided one after the other. Subsequently, the information of the two different measuring systems has to be related to the same spot on the surface. Calibration measurements on known objects or samples may be performed to serve this purpose.

Preferably, a control and evaluation unit will be provided. This unit is, however, spatially removed from the optical measuring system. This permits the device according to the invention to be kept as compact as possible. Furthermore, it is particularly important for the process-oriented quality surveillance to reduce to a minimum all factors which could lead to contamination.

The provision of two linear motors disposed on opposite sides of the sample holder has proven advantageous for stable operation. It is particularly preferred to connect these two linear motors by a carrier plate stretching across the sample holder and serving as support for the optical measuring system. This can give the optical measuring system the capability to move particularly gently.

In an additional preferred embodiment of the device according to the invention, a mechanism for the automatic adjustment of the distance of the optical measuring system from the sample surface to be measured is provided. This mechanism comprises an adjusting light source whose beam is directed toward the sample surface, a position-sensitive photo detector for detecting the reflected adjustment beam, as well as a control unit, and a distance adjustment unit for the adjustment of the distance between measuring head and sample surface.

An apparatus of this kind is proposed by the patent application U.S. Pat. No. 6,094,199 for ellipsometers. The measurement is performed according to the triangulation principle. Thanks to the automatic correction of the operating distance it becomes possible to measure even arched samples, although the depth of focus of the scattered light measuring device is approximately 100 micrometers.

An additional preferred embodiment of the device according to the invention comprises a mechanism for recognizing a notch in the sample to be measured. For this purpose, the mechanism is equipped with a laser with a band-shaped laser beam which is directed toward the sample surface, as well as with a detector for measuring the reflected beam.

Preferably, an alignment mechanism is also provided which is equipped with a vertically movable, driven sample table which is disposed in the rotational axis of the sample holder and can be rotated. It is advantageous for the drive mechanism of the sample table to be linked to a control mechanism which is connected to the notch detection mechanism. This makes it possible to align the sample to be measured accurately in each case by hand or automatically.

Preferably, a light deflecting unit is placed downstream from the light source. If this light deflecting unit is disposed at the same angle as the scattered light deflecting unit, light source and photo detector can be placed side by side, which makes a very compact construction of the optical measuring system possible It may also be advantageous to dispose a light wave guide downstream from the light source. This allows the light source as such to be spatially removed from the other components of the optical measuring system. In this way, the optical measuring system can be miniaturized and/or be designed in compact construction without becoming subject to excessive limitation in the selection of the light source. The use as light wave guide also makes it easier to set up any kind of incidence geometry in the proximity of the sample. Downstream from the light wave, as well, a light deflecting unit may be provided.

In order to show the scattered light signal on the photo detector, a focusing unit, e.g. a lens, may be disposed between the scattered light deflecting unit and the photo detector. Due to the low intensity of the scattered radiation in this area, the probability of parasitic scattered light radiation is relatively small. Otherwise, the scattered light deflecting unit itself could also be constructed as focusing mechanism, e.g. by arching it.

In a preferred embodiment, additional optical elements are provided for additional measurements. These need not be complete optical measuring systems. By arranging the additional elements, for example, in the individual channels of a turret-like housing part, the already existing light source and photo detector can be used for additional measurements.

BRIEF DESCRIPTION OF THE DRAWINGS

The invention is described in detail with the aid of the following drawings.

DETAILED DESCRIPTION OF THE INVENTION

Figure 1:
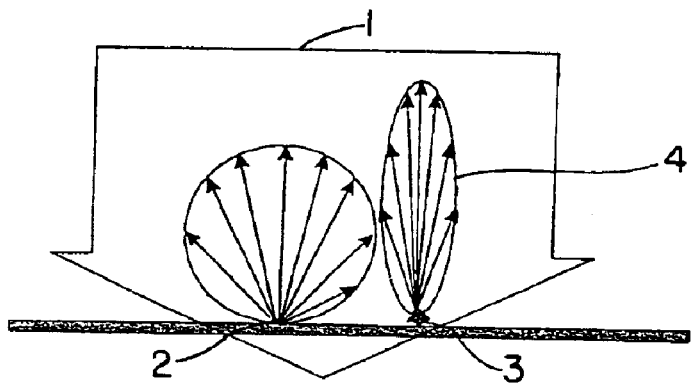
FIG. 1 shows the different scatter characteristics of particles.

FIG. 1 shows the differing scatter characteristics of particles of differing sizes. Incident light 1 falls on a small particle 2 as well as on a large particle 3. A particle is considered small when its size is much smaller than the wavelength of the incident light 1. A particle is considered large when its size is comparable to the wavelength of the incident light 1 or even greater. The scatter characteristics of small particles 2 and large particles 3 differ in so far as the small particle 2 scatters in isotropic manner into the space, while the large particle 3 generates strong backscattering.

Figure 2:
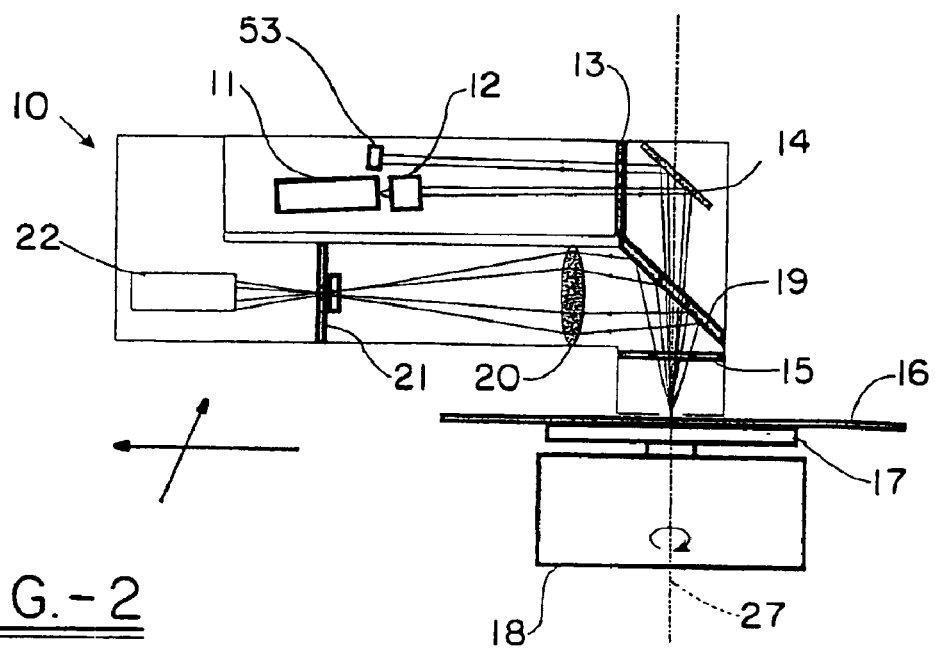
FIG. 2 shows an optical measuring system for the detection of large particles.

FIG. 2 shows an optical measuring system for the detection of large particles in the form of a measurement block 10 for measuring samples such as wafers 16. The wafer 16 is supported by a sample holder (wafer chuck) 17 which is caused by a rotation motor 18 to rotate around the axis 27 perpendicularly to the wafer surface 16. The arrows indicate the possible directions of movement of the optical measurement block 10. Due to the overlap of the translational movement of the measurement block 10 and the rotational movement of the wafer surface 16, each spot on the wafer surface 16 can be measured.

A laser 11 serves as light source. The light beam first traverses a beam-shaping optical system 12 and a diaphragm 13, before hitting the laser deflection mirror 14 and being reflected onto the sample surface. Not only the incident beam, but also the reflected beam pass the signal deflection mirror 19 and the diaphragm 15 by traversing the respective openings. The isotropic scattered light generated by any possible small particles is blanked out by the diaphragm 15. Only the back scatter caused by large particles traverses the diaphragm 15 and is deflected at the signal deflection mirror 19 onto the photo multiplier 22. In order to focus the scattered light and to improve the signal-to-noise ratio, the scattered light traverses the lens 20 and the third diaphragm 21. The incident beam is not projected onto the sample surface exactly vertically, but rather at a very small angle to the surface normal line so that the reflected beam, as well, can be monitored with the aid of the photo detector 53. Furthermore, this allows the reflectivity of the sample surface also to be measured.

Thanks to a particular optical system, especially the diaphragm 15, the optical measurement block 10 shown in FIG. 2 ensures that predominantly the backscatter of large particles is detected. By using only mirrors and diaphragms upstream from the sample surface and in the proximity of the surface, it can be ensured that parasitic scattering is minimized and that the signal-to-noise ratio is optimized. Another advantage is represented by the compact construction of the measurement block 10 as made possible by the deflection mirrors 14 and 19.

Figure 3A:
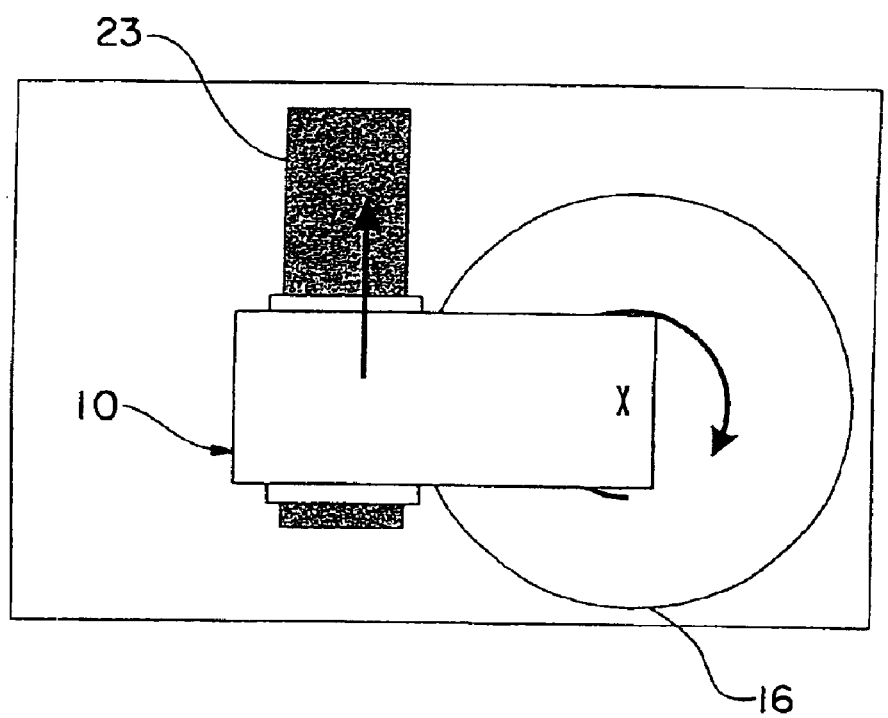
FIG. 3a,b show an embodiment of the device according to the invention.
Figure 3B:
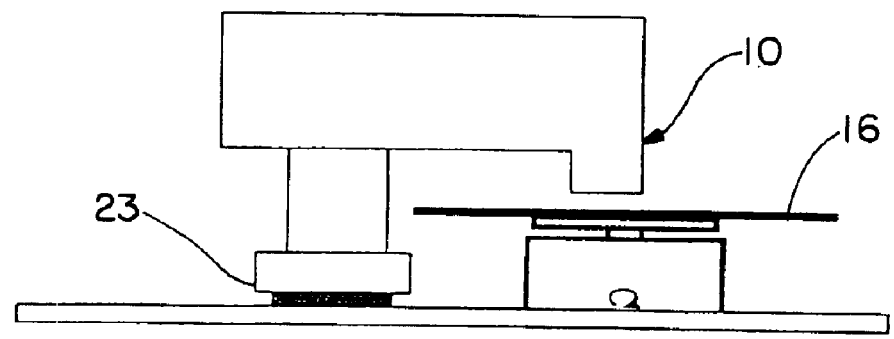

FIG. 3a shows a top view of the device according to the invention, while FIG. 3b shows a side view. The measurement block 10 is supported by a linear motor 23 and thereby is moved radially outward from the center of the wafer 16, while the wafer 16 is caused to enter into a quick rotation. The movements of the two drives are balanced in such a way that the entire surface is scanned on a spiral path. The translational movement of the measurement block 10 radially to the wafer edge is particularly important when the measuring spot (in FIG. 3, indicated by the cross) itself is anisotropic, as for example, the beam profile of a diode laser. In this case, the long axis of the measuring spot should be radially aligned.

Figure 4A:
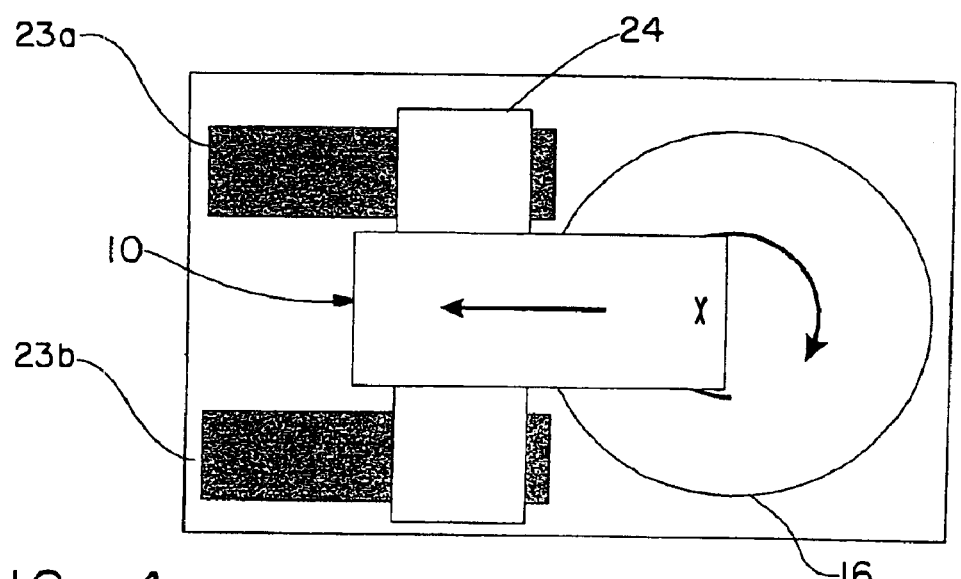
FIG. 4a,b show an additional embodiment of the device according to the invention.
Figure 4B:
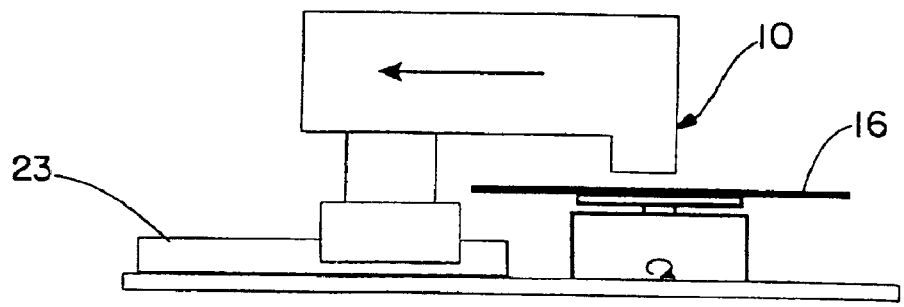

FIGS. 4a and 4b show a variation of the device according to the invention, wherein the measurement block 10 is supported by a bridge, which in turn is supported by two linear motors 23. Here again, the measurement block 10 is moved radially outward from the center of the wafer 16 with the aid of the linear motors 23, while the wafer 16 is caused to enter into a quick rotation.

Figure 5A:
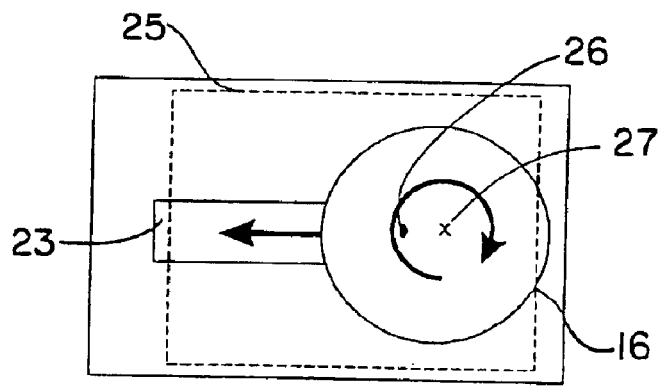
FIG. 5a shows the operation of the device according to the invention.
Figure 5B:
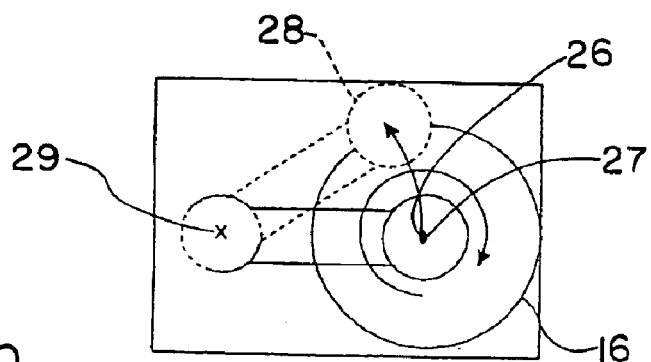
FIG. 5b shows the operation as based on the state of the art.

FIG. 5a shows once more the operation of the device according to the invention. The measurement block 25 which generates a measuring spot 26 is supported by the linear motor 23 and is moved radially to the rotational axis 27 of the wafer 16. Only an insignificant amount of more space is needed than for the device schematically shown in FIG. 5b which operates on the basis of the record player principle. The measuring head 28, which is very small, is attached to one end of an arm and is guided over the rotating wafer around the rotational axis 29. In spite of the comparable spatial needs, the measurement block 25 according to FIG. 5a can accommodate a much more complex optical system and/or larger components, such as a blue light laser.

Figure 6A:
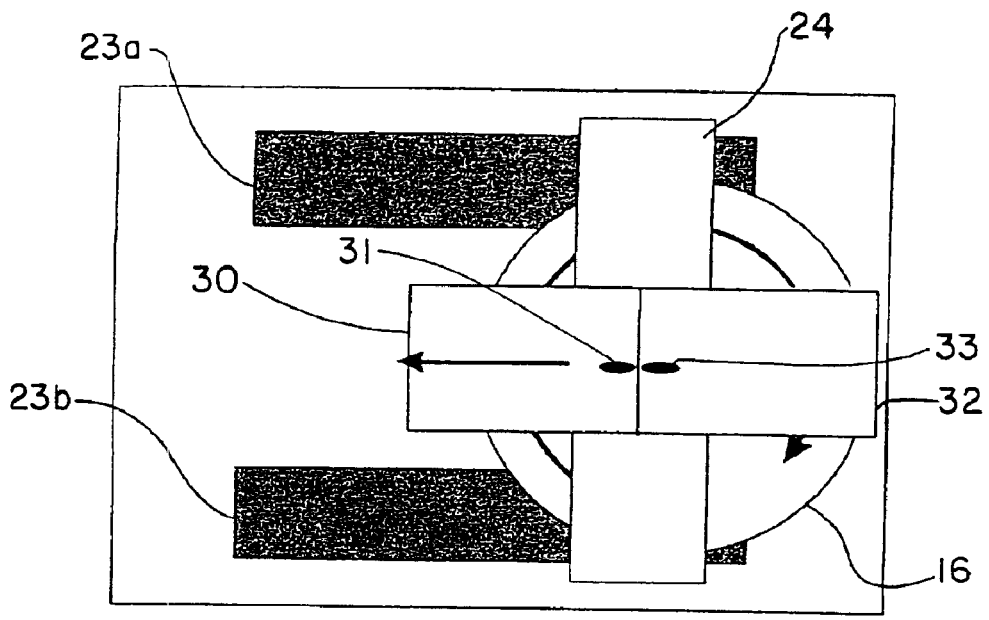
FIG. 6a,b show a particularly preferred embodiment of the device according to the invention.
Figure 6B:
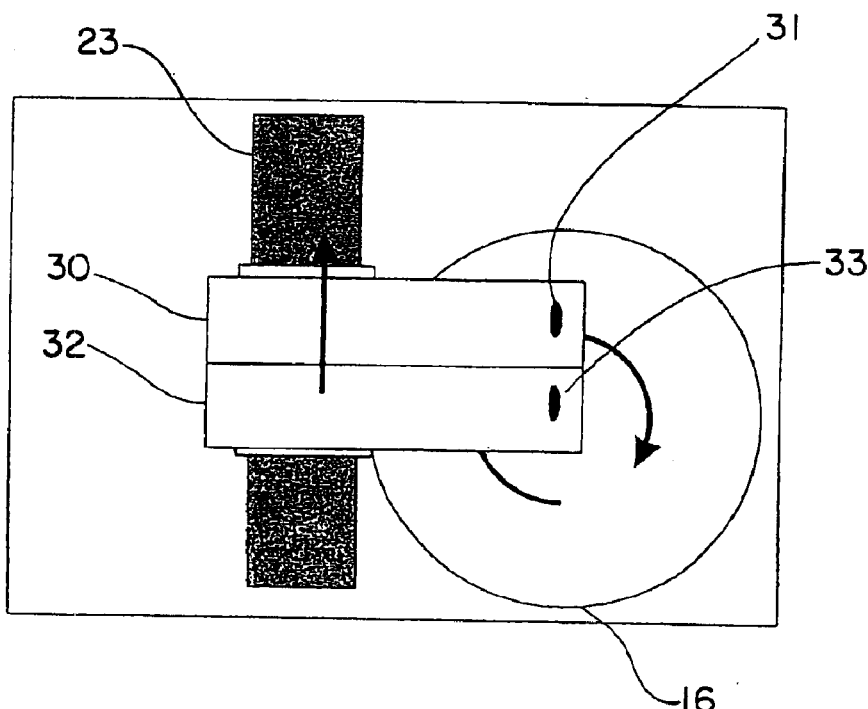

In a preferred embodiment shown in FIG. 6a in a first variation and in FIG. 6b, in a second variation, it becomes clear how the new space can be used effectively. Two measurement blocks 30 and 32 are disposed next to one another in a fixed relation. The two measurement blocks 30, 32 generate elliptical measuring spots 31, 33 which are disposed radially to the wafer surface 16 and are moved radially outward with the aid of the two linear motors in FIG. 6a, and with the aid of the one linear motor 23 in FIG. 6b.

This modular model makes the combination of two or more detection channels on one and the same apparatus possible. The results for the two channels for one measuring spot are received one after the other. The information of the two channels has to be brought into the appropriate relation by means of a calibration measurement on a known object or pattern. The second measurement block 32 could be a measurement block for measuring scattered light for small particles, as described below in FIG. 7. It could also, for example, be a dark field microscope. This would bring an additional manner of illuminating the surface into play which would provide additional information, e.g. with regard to the question whether external particles or embedded particles or indentations are being targeted. Furthermore, the second measurement block 32 may also be a spectrometer for measuring layer thickness. Any conceivable combination of measurement blocks may be used in the construction of the devices shown in FIGS. 6a,b.

Figure 7:
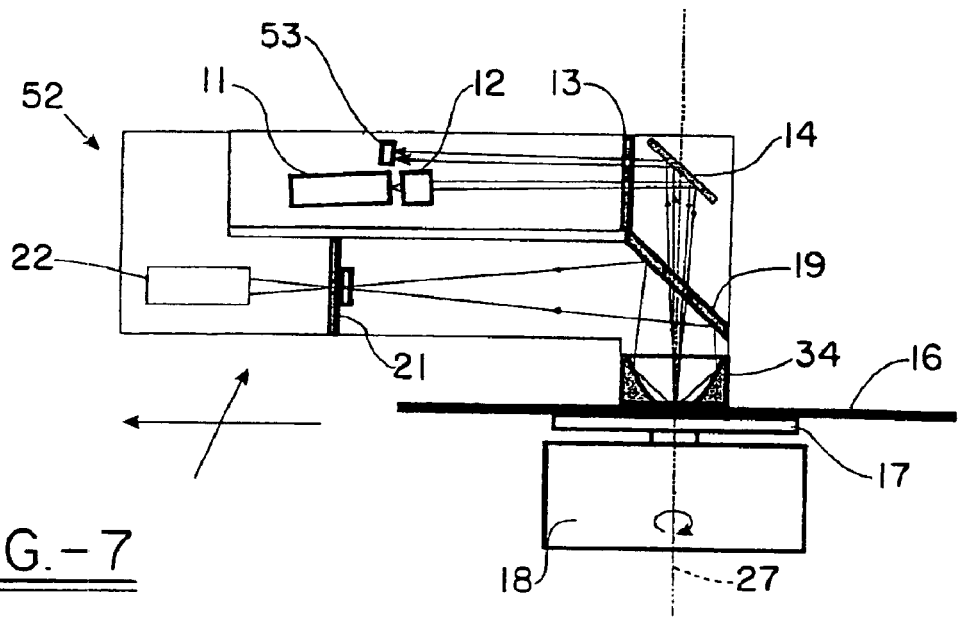
FIG. 7 shows an additional measuring system.

FIG. 7 shows an example of a second measurement block 52 in the form of a measuring apparatus for measuring the scattered light component of small particles. It differs from the first measuring configuration 10 (FIG. 2) only in so far as an elliptical mirror 34 replaces the diaphragm 15 in the proximity of the surface and collects the light scattered in isotropic manner, projects it onto the deflection mirror 19, and from there, through the diaphragm 21 onto the photo multiplier 22. Since the mirror 34 itself is focused already, an additional focusing element, such as the lens 20 in FIG. 2, is not needed. The fact that no refractive optical systems at all are used in the area of the ellipsoid mirror ensures a low degree of parasitic scattered light. This leads to a very good signal-to-noise ratio.

Figure 8:
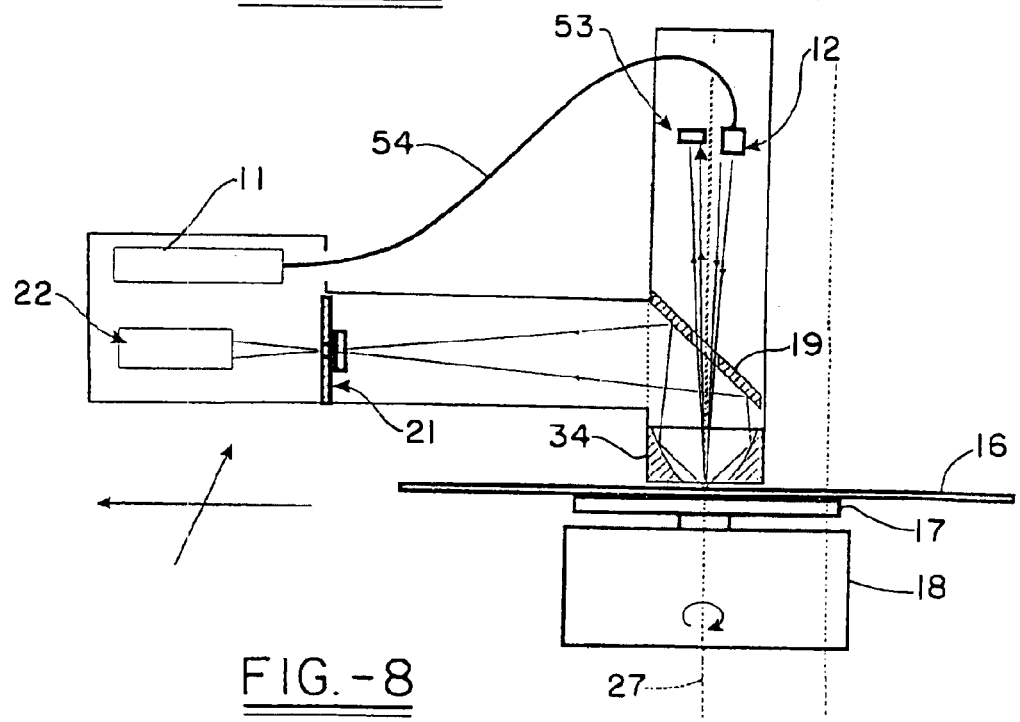
FIG. 8 shows an additional measuring system.

FIG. 8 shows an optical measuring system, wherein the laser 11 is located somewhat removed from the actual optical measuring system and its light is projected to the desired area of the measuring system via a light wave guide 54. The example shown here, therefore, can do without the laser deflection mirror. This permits a slight improvement of the signal-to-noise ratio and/or a slight increase in the intensity of the scattered light signal. Furthermore it is possible that the laser 11 as well as the photo multiplier 22 have to be cooled during operation. This can occur simultaneously without negatively influencing the actual measurement.

Figure 9A:
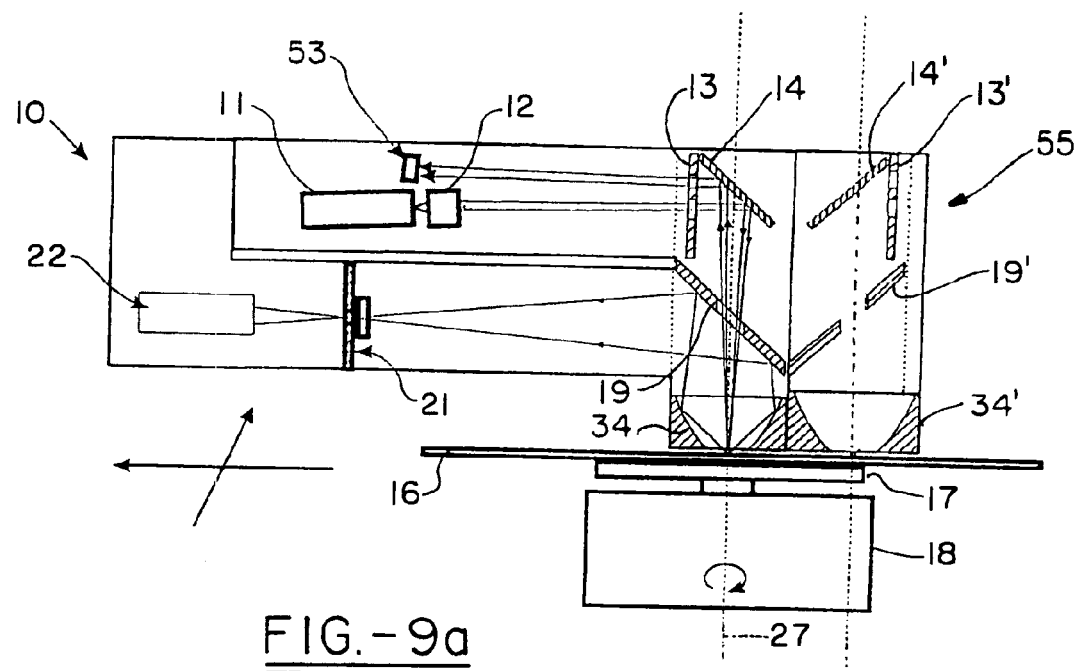
FIG. 9a,b show an additional measuring system.
Figure 9B:
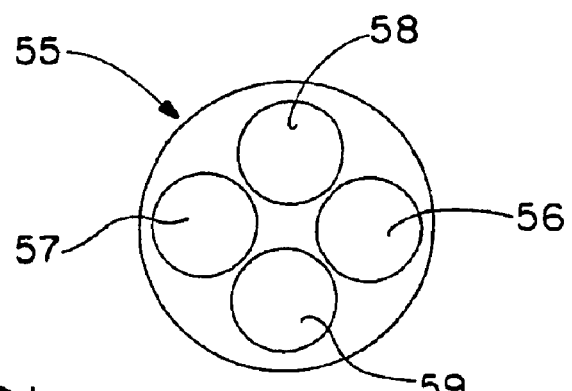

In FIG. 9a, the optical measuring system is placed in a turret 55. The turret 55 is schematically shown in a top view in FIG. 9b. It comprises four channels 56, 57, 58, 59. Channels 57 and 56 contain measuring systems for a second and a first scattered light measurement. These are shown in cross section in FIG. 9a. Channel 58 contains a camera. Channel 59 is still unassigned. The optical systems for deflection and collection 14, 14', 19, 19', 34, 34' as well as the diaphragms 13 and 13' of the two channels 57 and 56 all use, as needed, the light source 11 with a beam-shaping optical system 12 of the measurement block 10 as well as the photo multiplier 22 and the diaphragm 21. In the present case, the two ellipsoid mirrors 34 and 34' have differing dimensions so that differing portions of the scattered light are collected. Instead of the ellipsoid mirror 34, paraboloid mirrors could also be used.

Figure 10:
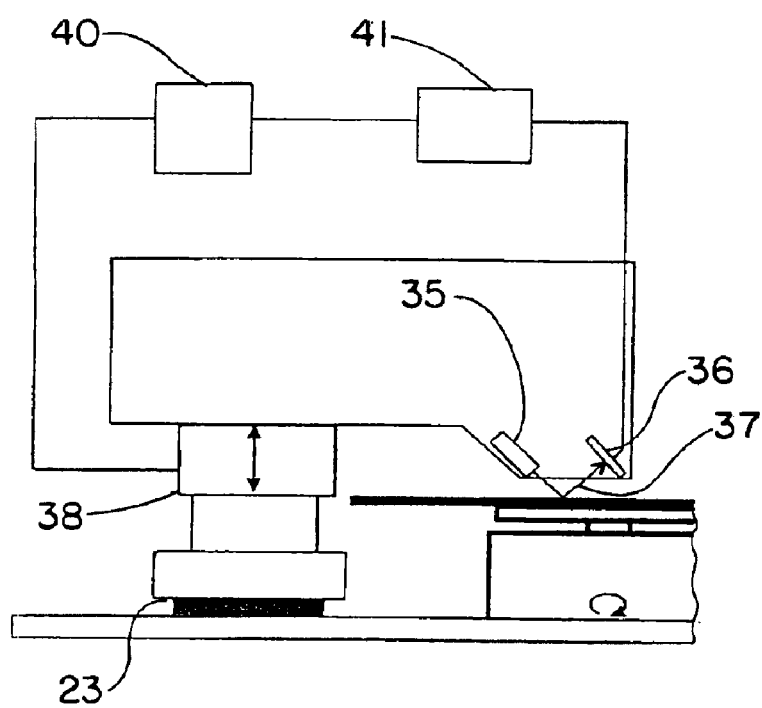
FIG. 10 shows a device for the automatic distance adjustment.

FIG. 10 shows an automated system for distance adjustment. A laser triangulation sensor, consisting of an adjustment laser 35 and a position-sensitive detector 36, is placed at the exit of the optical apparatus of the measurement block. The adjustment laser beam 37 is projected onto the wafer surface at a slant, e.g. less than 45 degrees. After reflection, the beam hits the position-sensitive detector 36. The position of the laser beam 37 on the position-sensitive detector 36 is a measure for the distance between the beam spot and the measurement block. The height of the measurement block can be adjusted with the aid of a linear motor 38. When adjusting the working spot of the scattered light detector, the optimal working distance is found by optimizing the scattered light signal. Subsequently, the associated incidence point of the adjusting laser beam 37 on the position-sensitive detector 36 is determined and provided to a computer or an electronic control system 41 as reference point. If the working distance changes during the translational movement of the measurement block, this is detected by the position-sensitive detector and a corresponding control signal is generated. Based on this control signal, the distance of the measurement block is automatically corrected with the aid of the height adjusting motor 38 and the motor driver 40.

Figure 11A:
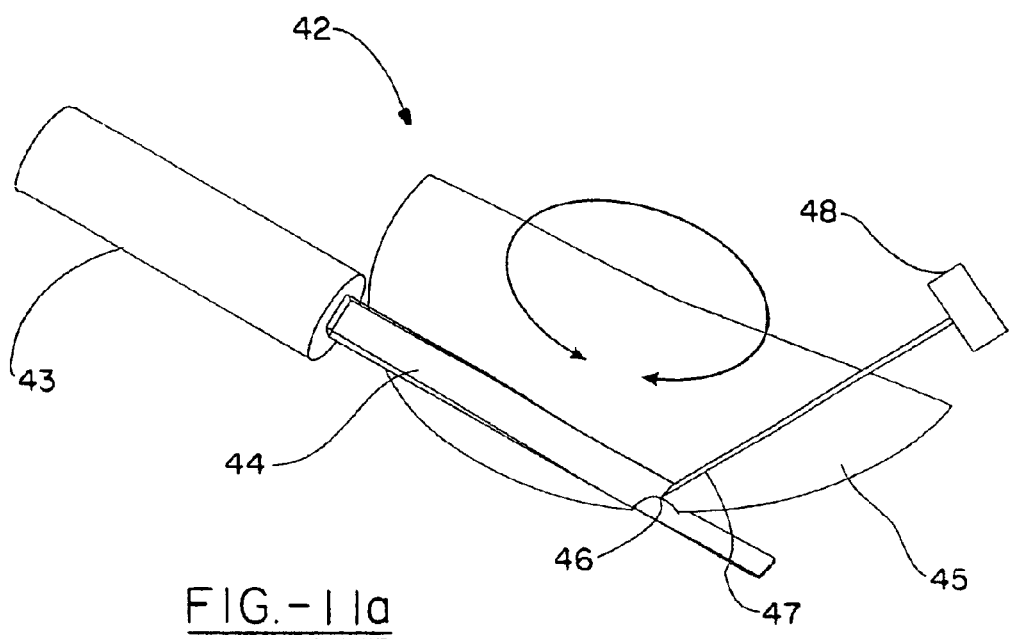
FIG. 11a,b show a notch detection unit.
Figure 11B:
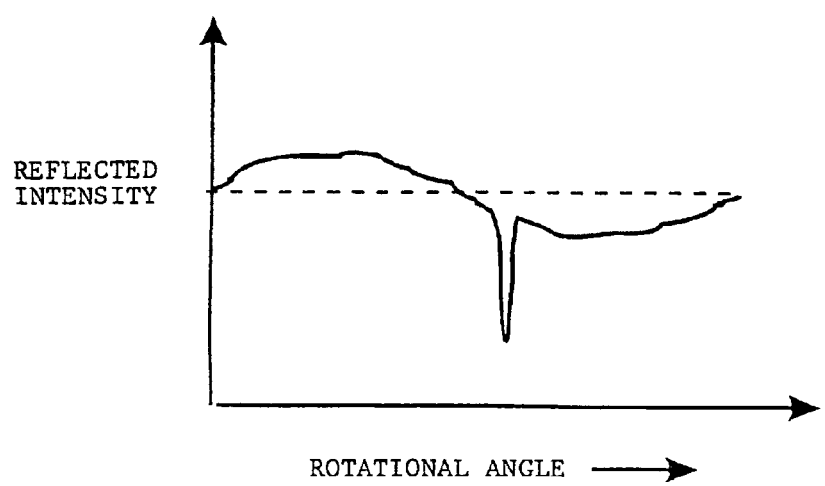

FIG. 11a schematically represents the notch detection system 42. The wafer 45 has a notch 48 toward which a laser 43 is directed. The laser beam 44 used here is band-shaped and directed toward the edge of the wafer 45. The reflected beam is marked as 47 and the associated detector in the form of a photo diode, as 48. When during the rotation of the wafer 45, one part of the band-shaped laser beam 44 is reflected from the wafer surface, the intensity of the reflected beam 47 drops precipitously as soon as the beam reaches the notch 45, as shown in FIG. 11b. A signal is received which is periodic over 360 degrees and whose period and phase length provide information about the position of the center of the laser in relation to the rotational axis of the wafer table. A deep cut generated by scanning the notch 46 is superimposed on the periodic signal. From this signal and the associated signal of an angle sensor which is not shown, the position of the notch and thus also the orientation of the wafer can be deduced.

Figure 12A:
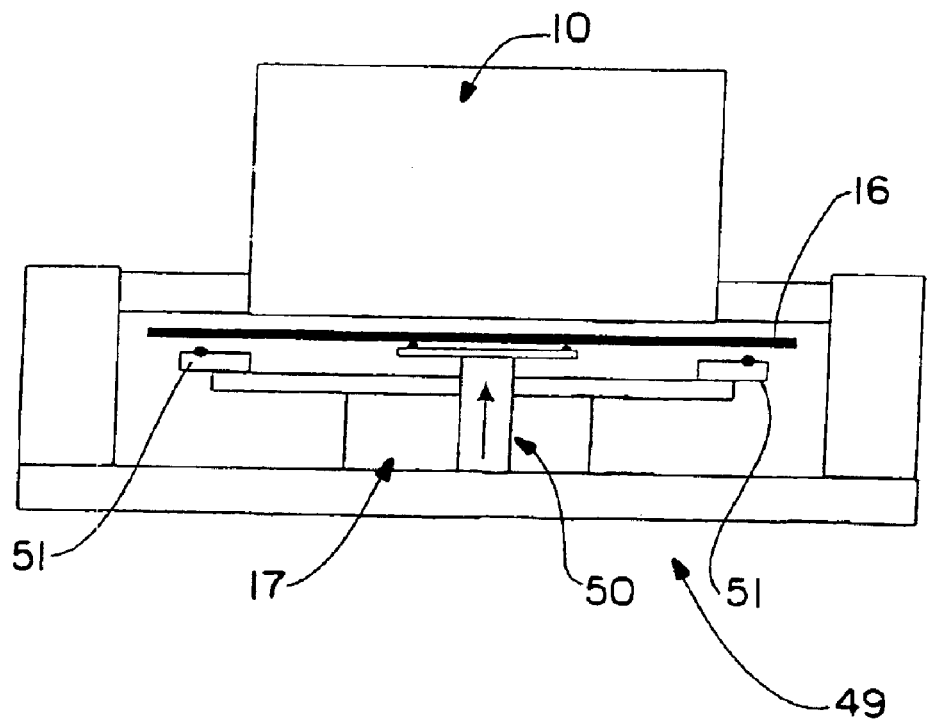
FIG. 12a,b show an alignment unit.
Figure 12B:
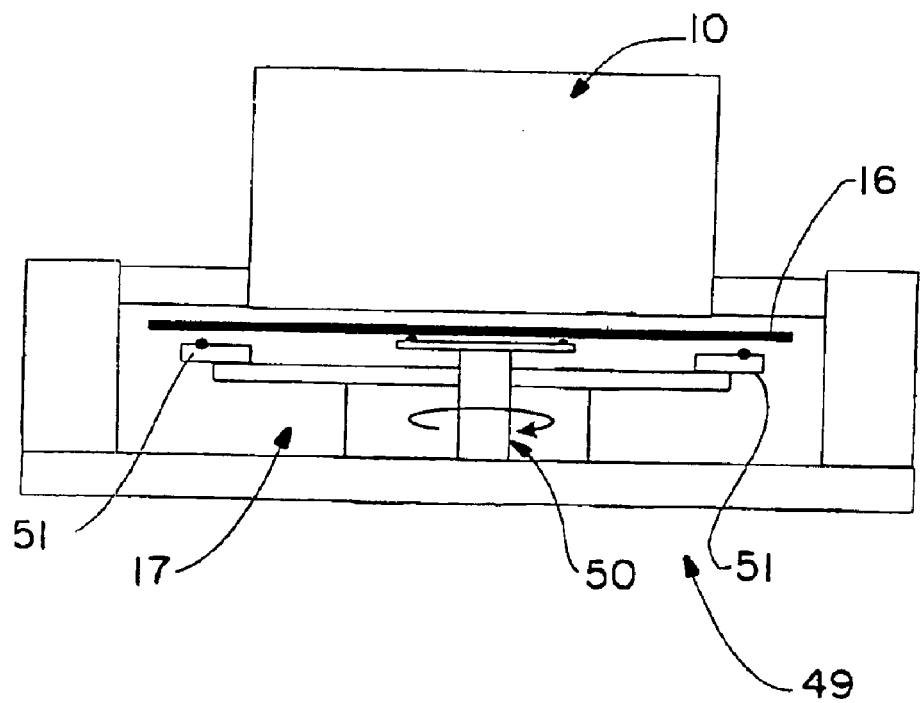

FIGS. 12a and 12b show the wafer alignment mechanism 49 (notch aligner) associated with the notch detector system 42. The alignment mechanism 49 is centered within the cup-shaped sample holder 17. The wafer is resting thereon in an elevated state. By rotating the wafer alignment mechanism based on the information provided by the notch detection system, the wafer 16 can be aligned correspondingly and subsequently again be placed on the supporting edge 51. The wafer lifter 50 can at any time consist of a simple lifting system and comprise, for example, a plunger-type coil drive or a stepping motor. The alignment mechanism and the mechanism for detecting notches are actively connected with one another by the fact that the drive mechanism of the sample lifting table is connected to a control mechanism which in turn is connected to the notch detection mechanism.

List Reference Characters 1 incident light
2 small particle
3 large particle
4 scatter ellipse
10 optical measurement block
11 laser
12 optical system for shaping the beam
13 13' diaphragm 1
14 14' laser deflection mirror
15 diaphragm 2
16 sample
17 sample holder
18 rotation motor
19 19' signal deflection mirror
20 lens
21 diaphragm 3
22 photo multiplier
23a,b linear motor
24 carrier plate
25 measurement block
26 measuring spot
27 rotational axis
28 measuring head
29 rotational axis measuring head
30 measurement block 1
31 measuring spot 1
32 measurement block 2

33 measuring spot 2
34 34' ellipsoid mirror
35 adjustment laser
36 position-sensitive detector
37 adjustment laser beam
38 adjustment motor
39 linear motor
40 motor driver
41 electronic control system
42 notch detection mechanism
43 laser
44 band-shaped laser beam
45 wafer
46 notch
47 reflected beam
48 photo diode
49 alignment mechanism
50 sample lifting table
51 ring-shaped supporting edge
52 optical measurement block
53 photo detector
54 light wave guide
55 turret
56 scattered light channel No. 1
57 scattered light channel No. 2
58 camera channel
59 free channel

What is claimed is:

1. A device for measuring surface defects comprising
a sample holder;
a rotation drive for the sample holder, wherein the rotational axis of said rotation drive is perpendicular to a sample surface to be measured;
an optical measuring system for scattered light measurements with a light source whose light beam is projected onto a surface to be measured, with a deflecting unit for any scattered light possibly generated on the surface to be measured, as well as with a photo detector;
at least one linear drive for the measuring system, wherein a translational direction of said linear drive is radial to the rotational axis of the sample holder; and
a second measuring system for measuring any additional physical property, wherein both measuring systems are disposed at an unchangeable distance from one another and are located one behind the other in translational direction.

2. A device according to claim 1, wherein a control and evaluation unit spatially removed from the optical measuring system is provided.

3. A device according to claim 1, wherein the linear drive comprises two linear motors positioned on two opposite sides of the sample holder.

4. A device according to claim 3, wherein two linear motors are connected via a carrier plate which stretches across the sample holder and serves as support for the optical measuring system.

5. A device according to claim 1, with a mechanism for the automated adjustment of the distance between the optical measuring system and the sample surface to be measured, comprising
an adjustment light source whose beam is directed toward the sample surface to be measured;
a position-sensitive photo detector for detecting the reflecting adjustment beam; as well as
a control unit and a distance adjustment mechanism, in order to adjust a distance between measuring head and sample surface.

6. A device according to claim 1, with a mechanism for detecting a notch in the sample to be measured, comprising a laser with a band-shaped laser beam directed toward the sample surface, and a detector for measuring the reflected beam.

7. A device according to claim 6, comprising an alignment mechanism equipped with a vertically movable, rotatable, driven sample lifting table disposed in the rotational axis of the sample holder.

8. A device according to claim 7, wherein the drive mechanism of the sample lifting table is connected to a control mechanism which is connected to a notch detection mechanism.

9. A device according to claim 1, wherein a diaphragm for adjusting the acceptance angle of the scattered light is placed upstream from the scattered light deflecting unit .

10. A device according to claim 1, wherein the light beam of the light source falls essentially perpendicularly onto the surface to be measured.

11. A device according to claim 1, wherein a light deflecting unit is placed downstream from the light source.

12. A device according to claim 1, wherein a light wave guide is placed downstream from the light source.

13. A device according to claim 1, wherein a focusing unit is placed between the scattered light deflecting unit and the photo detector.

14. A device according to claim 1, wherein the scattered light deflecting unit is constructed as a focusing unit.

15. A device according to claim 1, wherein the scattered light deflection unit is constructed as a mirror which has an opening for the incident and the reflected light beams.

16. A device according to claim 1, wherein additional optical elements are provided for additional measurements.

17. A device according to claim 1, wherein the additional optical elements are placed in the individual channels of a turret-like housing part.

18. A device according to claim 1, wherein a focusing mirror is placed between a light deflecting unit and the scattered light deflecting unit in order to collect the scattered light.

* * * * *